(12) United States Patent
Davis

(10) Patent No.: US 6,936,020 B2
(45) Date of Patent: Aug. 30, 2005

(54) ORTHOPEDIC SPLINT

(76) Inventor: Perry H. Davis, 426 Martinique Cove, Niceville, FL (US) 32578

( * ) Notice: Subject to any disclaimer, the term of this patent is extended or adjusted under 35 U.S.C. 154(b) by 71 days.

(21) Appl. No.: 10/750,124

(22) Filed: Dec. 31, 2003

(65) Prior Publication Data

US 2004/0158184 A1 Aug. 12, 2004

Related U.S. Application Data

(60) Provisional application No. 60/440,559, filed on Jan. 16, 2003.

(51) Int. Cl.$^7$ .................................................. A61F 5/00
(52) U.S. Cl. .......................... 602/16; 602/26; 602/20; 602/62; 128/878; 128/882
(58) Field of Search ................................. 602/16, 5, 23, 602/24, 26, 20, 62; 128/845, 869, 878, 882, 103.1, 123.1; 623/39; 16/54

(56) References Cited

U.S. PATENT DOCUMENTS

| | | |
|---|---|---|
| 1,847,823 A | 3/1932 | Dresser |
| 2,646,793 A | 7/1953 | Swiech et al. |
| 4,180,870 A | 1/1980 | Radulovic et al. |
| 4,433,679 A | 2/1984 | Mauldin et al. |
| 4,493,316 A | 1/1985 | Reed et al. |
| 4,508,111 A | 4/1985 | Hepburn |
| 4,790,300 A | 12/1988 | Marx |
| 4,790,301 A | 12/1988 | Silfverskiold |
| 4,817,588 A | 4/1989 | Bledsoe |
| 5,036,837 A | 8/1991 | Mitchell et al. |
| 5,213,094 A | 5/1993 | Bonutti |
| 5,328,446 A | 7/1994 | Bunnell et al. |
| 5,385,534 A | 1/1995 | Cassford |
| 5,437,619 A | 8/1995 | Malewicz et al. |
| 5,472,412 A * | 12/1995 | Knoth ............... 602/26 |
| 5,624,386 A * | 4/1997 | Tailor et al. ............ 602/16 |
| 5,672,152 A * | 9/1997 | Mason et al. .......... 602/26 |
| 5,707,347 A * | 1/1998 | Bixler .................. 602/26 |
| 5,823,931 A * | 10/1998 | Gilmour ............... 602/24 |
| 5,954,678 A | 9/1999 | Cruz |
| 6,024,713 A * | 2/2000 | Barney ................ 602/23 |
| 6,179,799 B1 | 1/2001 | Doran |
| 6,325,773 B1 * | 12/2001 | Opel .................... 602/26 |
| 6,666,837 B2 * | 12/2003 | Weihermuller ......... 602/16 |
| 6,770,045 B2 * | 8/2004 | Naft et al. ............ 602/16 |
| 6,821,261 B2 * | 11/2004 | Doty et al. ............ 602/5 |
| 2002/0035342 A1 | 3/2002 | Williams |

FOREIGN PATENT DOCUMENTS

| | | |
|---|---|---|
| ES | 546461 | 8/1985 |
| GB | 159422 | 3/1921 |
| WO | WO 01/72256 A1 | 10/2001 |

* cited by examiner

*Primary Examiner*—Fadi H. Dahbour
(74) *Attorney, Agent, or Firm*—J. Ronald Richebourg

(57) ABSTRACT

An orthopedic splint for a patient having a limb including an upper limb, a lower limb, and a joint therebetween, and being useful for therapeutically stretching the soft tissue of the limb. The orthopedic splint includes a flexible support member having a distal end and a proximal end thereof. A first contact pad is rotatably attached to the proximal end of said flexible support member and is disposed for distributing load to the underside of the upper limb. A second support pad attached to the distal end of said flexible support member is disposed for distributing load to the underside of the lower limb; and, a third support pad is attached to a fulcrum disposed near the center of the flexible support member and being disposed for distributing load to the topside of the upper limb and in close proximity to said joint. Accordingly, the orthopedic splint provides therapeutic traction to the limb while placing the limb in a self-aligning suspension sling arrangement.

29 Claims, 16 Drawing Sheets

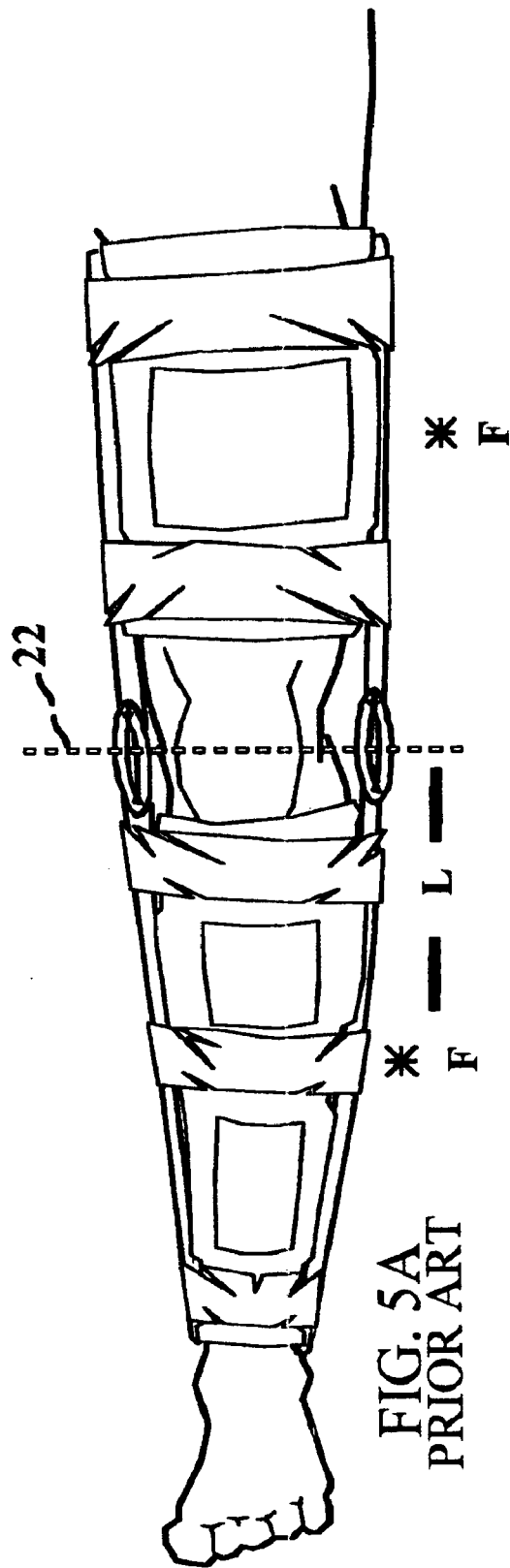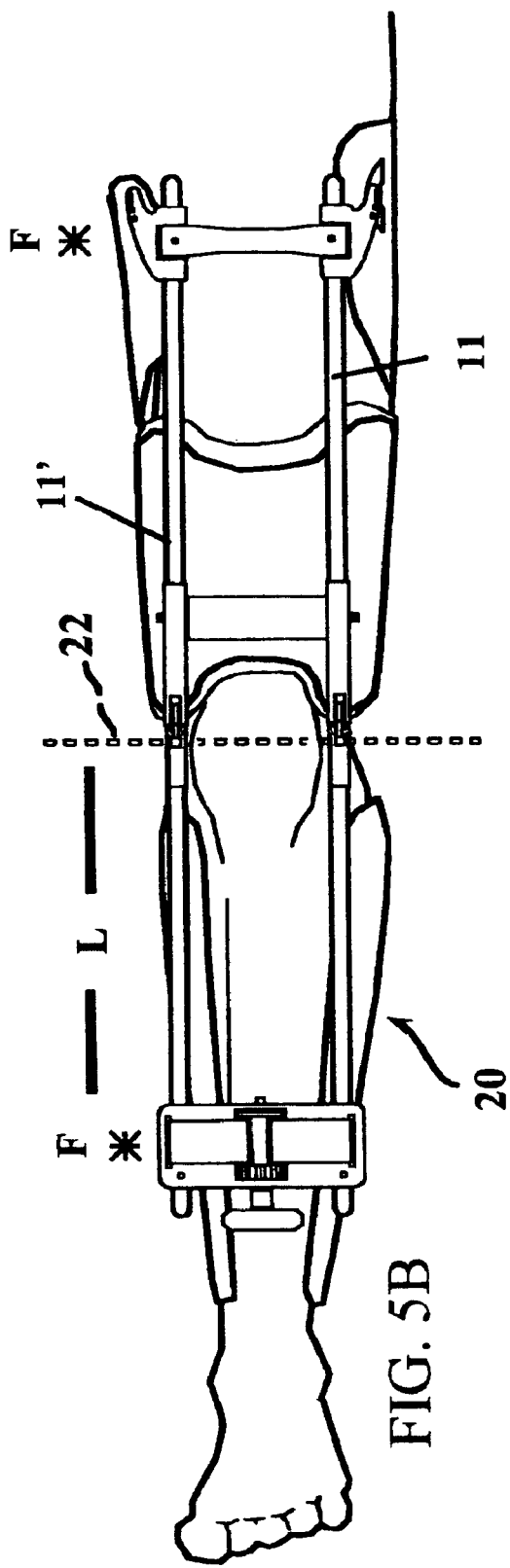
FIG. 5A
PRIOR ART
FIG. 5B

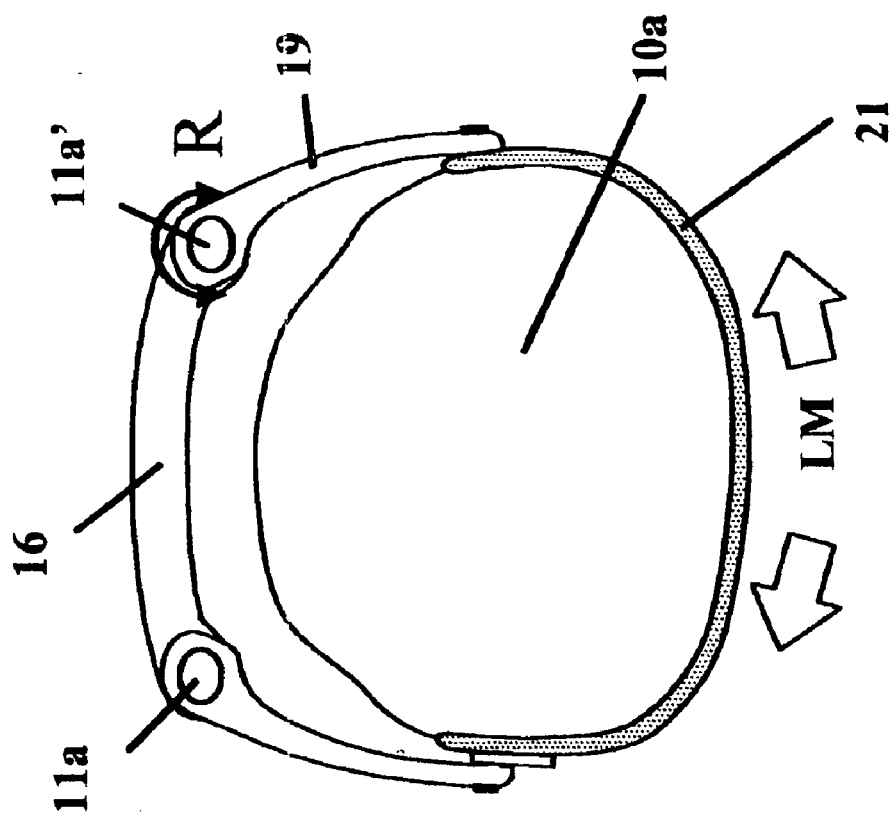
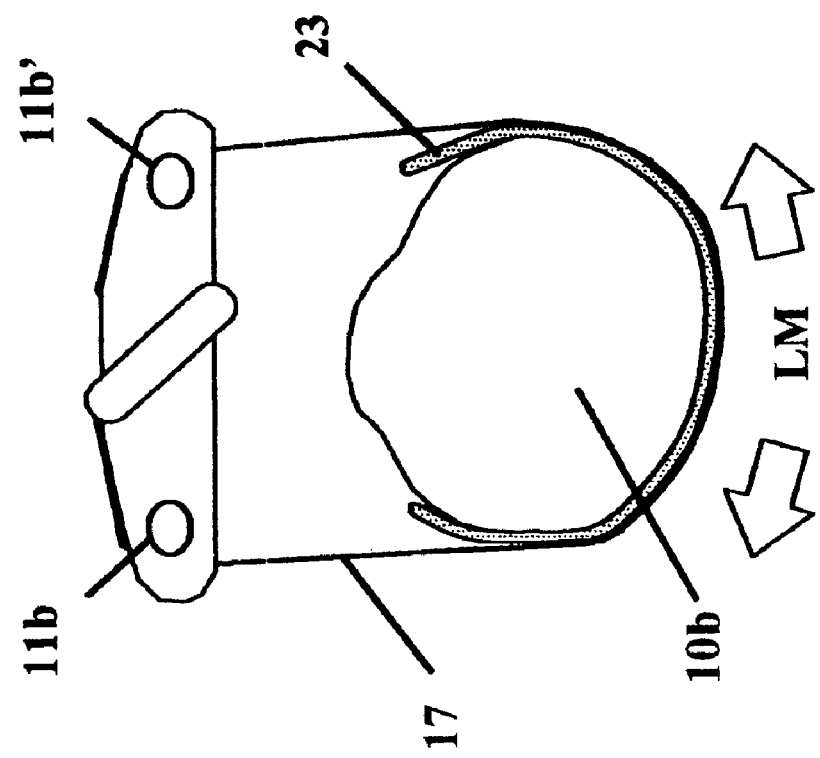

ORTHOPEDIC SPLINT

CROSS REFERENCE TO RELATED APPLICATION

This is a continuation application of Provisional Application No. 60/440,559, filed Jan. 16, 2003 by the same inventor hereof.

FIELD OF THE INVENTION

The present invention generally relates to orthopedic splints, and in particular to an improved orthopedic splint that is designed to prevent or reduce soft tissue contraction of the limbs or digits. The present invention provides an improved fit and function when compared with dynamic and static splint prior art made orthopedic splints.

BACKGROUND OF THE INVENTION

Neurological impairment, physical trauma, surgery or prolonged immobility frequently results in loss of range of motion due to contraction of the muscles, tendons and ligaments of the limbs or digits known collectively as "soft tissue". Soft tissue contraction can result in loss of range of motion of the limb in flexion or extension. Rehabilitation efforts to reduce or stretch such contractions usually involve extensive physical therapy or surgical intervention. Both physical therapy and surgical alternatives frequently include the use of some form of orthopedic splint. Such orthopedic splints are available as adjustable "off-the-shelf" devices or hand crafted custom orthotics molded to fit the individual patient or specific application. Although some splints may include attributes of both, orthopedic splints generally fall into one of two general categories known as static or dynamic.

Static splints are primarily designed to hold the limb or digits at a preset position and may be manually adjustable to accommodate different limb or digit positions. Static splints may be adjustable to fit off-the-shelf products or custom fitted orthotics. Serial casting is a form of static splinting where a series of casts hold the limb or digits in a succession of positions. Static splints are commonly used to restore range of motion, prevent the occurrence of soft tissue contraction associated with long term immobilization, hold limbs in the desired post-surgical position during healing, or as a mechanical support for ambulating.

Dynamic splints use components, such as springs or elastic bands, in order to provide an active tension as the soft tissues stretch, in essence "taking up the slack." As with static splints, dynamic splints may be off-the-shelf or custom made orthotics. Dynamic splints are designed to improve limb range of motion through exploiting the viscoelastic properties of soft tissues. When force is applied, soft tissues initially enter the elastic phase of stretch, a temporary condition wherein soft tissue returns to its previous state when force is removed. Under increased force or prolonged duration soft tissue enters the plastic phase of stretch where some permanent physical lengthening of the soft tissue is achieved. If the level of force or onset rate at which the force is applied is too great, soft tissue may be stressed beyond the intended plastic phase and may be torn or otherwise damaged. In order to achieve effective reduction of soft tissue contraction, it is imperative that a dynamic splint provide a precisely adjustable level of force that may be reliably reproduced and incrementally increased over successive therapy sessions. Of equal importance to the level of force applied is control of the direction and location at which force is applied. Misapplied force from a poorly designed or poorly fitting splint may force the limb outside the natural range of motion and de-stabilize the joint or cause permanent damage to the soft tissues.

Custom made orthotics are individually fabricated using molds taken from a patient's limb. Such orthotics generally offer superior fit and comfort through more uniform dispersion of pressure over the entire contact area of the splint. Such a custom fit may reduce some of the distortion problems found with off-the-shelf dynamic splints. Due to the labor intensive manufacturing process, custom orthotics are much more expensive than off-the-shelf splints and are not immediately available due to the extensive molding, manufacturing and fitting process required. Finally, custom orthotics are not easily adaptable and may require periodic replacement due to patient growth.

Generally, existing prior art is in the form of off-the-shelf splints. These pre-manufactured devices are often available in several standard sizes. Referring to FIG. 1, typically the rigid structural components 9 are fastened to a limb 10 via padding material 13 and 14, and a series of adjustable strap attachments 15 and 17. A variety of spring or elastic components are employed to provide force on the rigid structural components at a hinge point 19.

Referring to FIG. 2, the distortion of padding and strap attachments, when placed under stress S, result in twisting of the splint's strap attachments 15 and 17 at their intersections 12 and 14 with the rigid structural components 9. This twisting distortion allows the structural components 9 to shift from the desired alignment geometry, resulting in unintended joint stresses, and uneven distribution of pressure and constriction of the soft tissues of the limb 10.

Referring now to FIG. 3, the prior art structural components 9 and 9' follow the medial and lateral contours of the limb 10. Prior art structural components located medial and lateral to the limb require several angular changes A and A', for example, to conform to the contours of the limb 10. Prior art structural components are generally made of flat material with strength concentrated in a single vertical plane.

With reference now to FIG. 4, the flat structural components 9 and 9', while under stress or tension, are located medial and lateral to the limb 10 and they tend to twist (T) out of the desired alignment. As the structural components 9 and 9' (as well as 12 and 12') roll out of the desired vertical alignment, overall structural integrity of the splint is compromised due to the resulting flexing of the structural components, and distortion of the load paths. Other prior art devices compensate for this rolling effect by using heavier and more expensive structures such as tubing that is square in cross section.

SUMMARY OF THE INVENTION

Referring next to FIGS. 5A and 5B, a comparison between the prior art splint, described above, and splint 20 of the present invention, respectively, is shown in frontal views. With respect to the splint 20 of the present invention (FIG. 5B), which will be amplified further hereinbelow, orientation of attachments on flexible structural members 11 and 11' provide enhanced leverage L over the prior art device (FIG. 5A) by applying force F further down the limb 10, or further from the attached joint axis 22 of rotation. Concentration of force F further from the joint transfers proportionately more therapeutic force to the joint soft tissues for a given level of splint tension. The mechanical advantage gained enhances patient comfort by reducing contact pad pressure on the limb soft tissues. Accordingly, the present invention provides improved function and comfort over the prior art device due to structural orientation design with a "Floating Contact Pad". Furthermore, the unique floating support structure oriented superior to the surface of limb 10 in a fulcrum and lever arm configuration provides numerous improvements over the prior art.

The orthopedic splint of the present invention offers superior fit and function in applications with a user in order to reduce contraction in the soft tissues of a limb or digit. This unique design allows numerous improvements over currently available products. For example, a feature of the present invention provides for a safer, self-aligning design that ensures proper fit and comfort, thereby eliminating undesired joint stresses.

Another feature of the present invention resides in the provision of more precise control and measurement of dynamic force levels applied to a limb or digit of the user for measuring physical therapy progress.

Yet another feature of the present invention is the convenience and ease of use of the splint, which may be quickly donned or removed with two simple quick release fastenings.

Still another feature of the present invention is the ease with which more accurate application of dynamic forces may be applied in order to measure progress in sequential physical therapy sessions.

Another feature of the present invention is the ease and accuracy in replication of dynamic forces for sequential physical therapy sessions.

Yet another feature of the present invention is the provision of a modular design, which allows for custom fit, thereby eliminating the need for expensive and time consuming custom orthotics alternatives.

These features are realized through the use of one or more flexible support members oriented superior to the surface of a limb or digit. Flexible support members are oriented superior to the surface of a limb or digit. These flexible support members serve as the upper and lower moment arms of a lever attached to a fulcrum point located superior and in proximity to the limb joint. When placed under tension the lever and fulcrum arrangement of the flexible support members transfer force via attachments to contact pads on the opposing surface of the upper and lower portion of a limb or digit. The orientation of the flexible support members and fulcrum arrangement superior to a limb or digit allows flexion of the structural members, thereby placing the upper and lower portion of the limb in a suspension sling arrangement allowing natural lateral alignment. This self-alignment prevents splint distortion and eliminates misalignment stresses on the limbs. A dynamic tension adjustment mechanism attached to either or both ends of the flexible support members allows incremental adjustment of dynamic forces. An adjustable hinge on the flexible support member is located in near proximity to the limb joint. Such a hinge mechanism allows angular adjustment of the upper and lower sections of the flexible support member, thereby allowing for close alignment of the splint with the upper and lower portion of the limb, while retaining the desired flexible properties of the flexible support member.

The present invention offers significant advantages and improvements over the prior art devices. For example, an advantage of the present invention is the structural orientation superior to a limb.

Another advantage of the present invention is the use of flexible structural support members.

Still another advantage of the present invention is the use of an adjustable hinge and locking mechanism for the flexible support members.

Yet another advantage of the present invention is the provision of an adjustable tensioning device.

Another advantage of the present invention is the use of a modular splint design that allows customized fit and function from stock components.

Yet another advantage of the present invention is that it is fully compatible with Ankle Foot Orthotics (AFO) for reduction of heel cord contraction.

Still another advantage of the present invention is the superior ease of use of the orthopedic splint of the present invention.

Another advantage of the present invention is its superior structural orientation. That is, its orientation is superior to a limb surface, which allows for greater structural integrity, reduced structural weight and reduced manufacturing cost by eliminating the need for heavier components necessary to provide comparable strength.

The employment of stock components in a range of sizes coupled with a completely adjustable configuration offers superior comfort and functionality for a wide range of patients. These attributes offer the advantages of custom molded orthotics while eliminating the associated lengthy manufacturing delays, numerous fittings, and higher costs.

Modular design and adjustable configuration easily adapts to patient growth through individual component adjustment or replacement.

Still other features and advantages of the present invention will become readily apparent to those skilled in the art from the following detailed description, wherein is shown and described only the preferred embodiment of the invention, simply by way of illustration of the best mode contemplated for carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive, and what is intended to be protected by Letters Patent is set forth in the appended claims. The present invention will become apparent when taken in conjunction with the following description and attached drawings, wherein like reference numerals indicate like parts, and which drawings form a part of this application.

BRIEF DESCRIPTION OF THE DRAWINGS

FIGS. 5A and 5B show a side-by-side comparison of a typical prior art splint (FIG. 5A) under stress and the splint of the present invention (FIG. 5B) under tension.

FIGS. 9A and 9B illustrate the splint of the present invention in cross-section when attached to the lower and upper parts, respectively, of a limb.

DETAILED DESCRIPTION OF ONE EMBODIMENT

For descriptive clarity and continuity, illustrations depict the orthopedic splint of the present invention as applied to a lower limb of a human. Functionality and attributes of the present invention illustrated are not limited to a lower limb and apply equally in function and use to other limbs, extremities and digits of the human body. Though the illustrations and description depict two flexible support members 11 and 11', the invention is not limited to this structure. For example, one flexible support member may be used, however, two such members provide a more stable splint.

Figure 1:
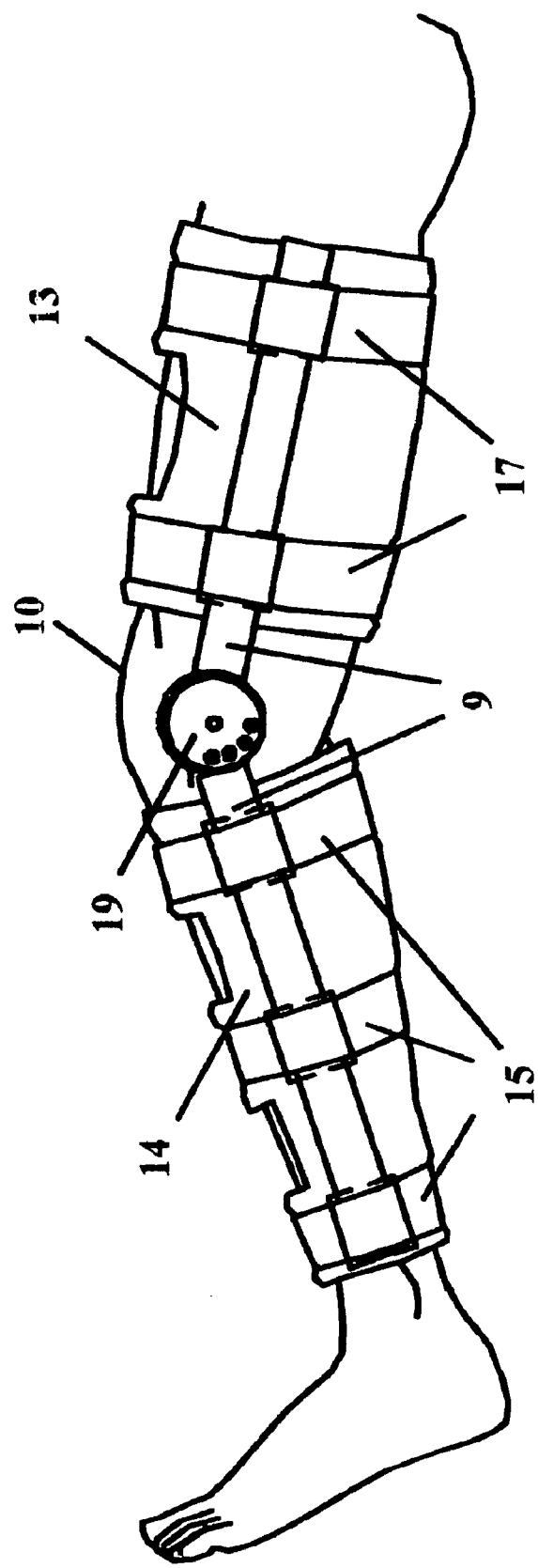
FIG. 1 is a side view of a typical prior art splint in a relaxed state.
Figure 2:
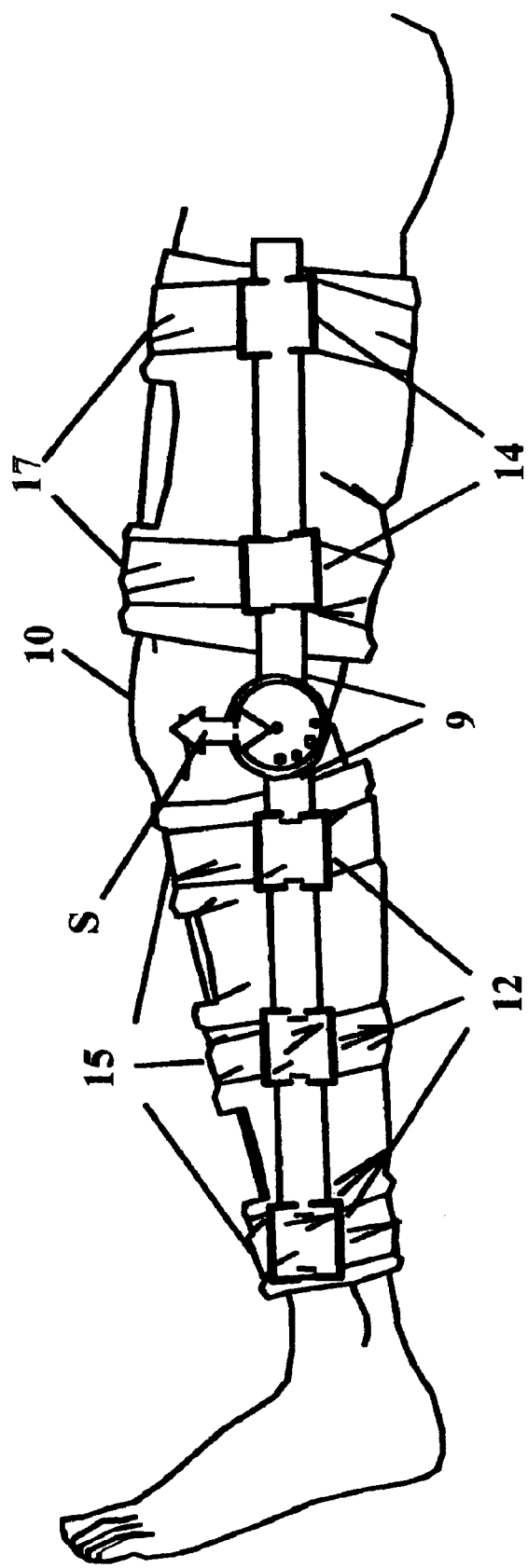
FIG. 2 is a side view of the prior art splint in a stressed state showing splint distortion and misalignment under load.
Figure 3:
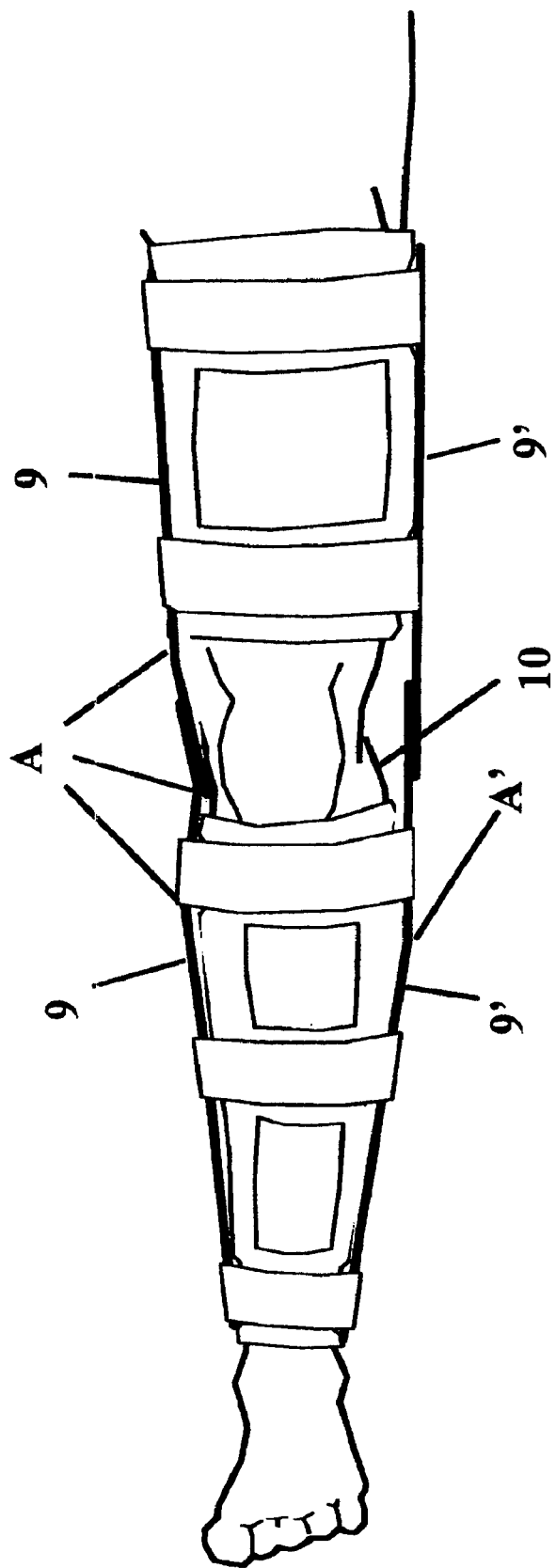
FIG. 3 is a top view of the prior art splint of FIG. 1 in a relaxed state.
Figure 4:
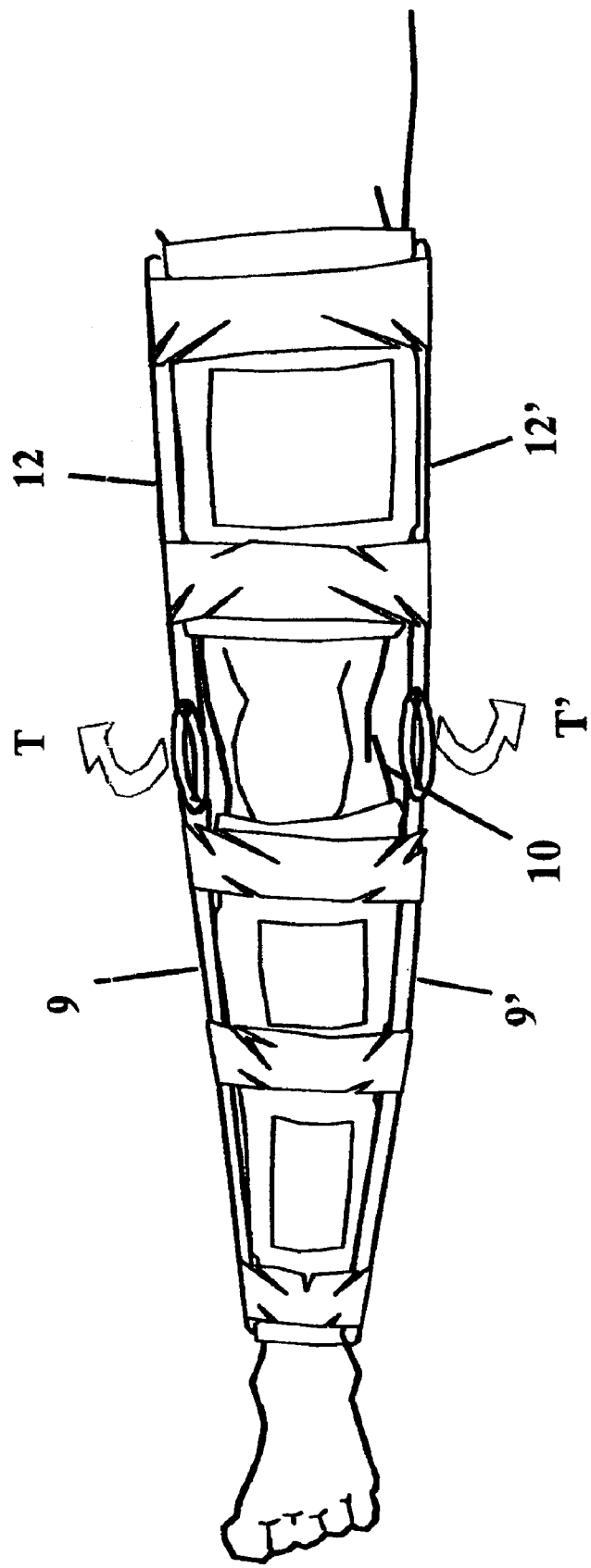
FIG. 4 is a top view of the prior art splint of FIG. 1 in a stressed state.
Figures 6A, 6B:
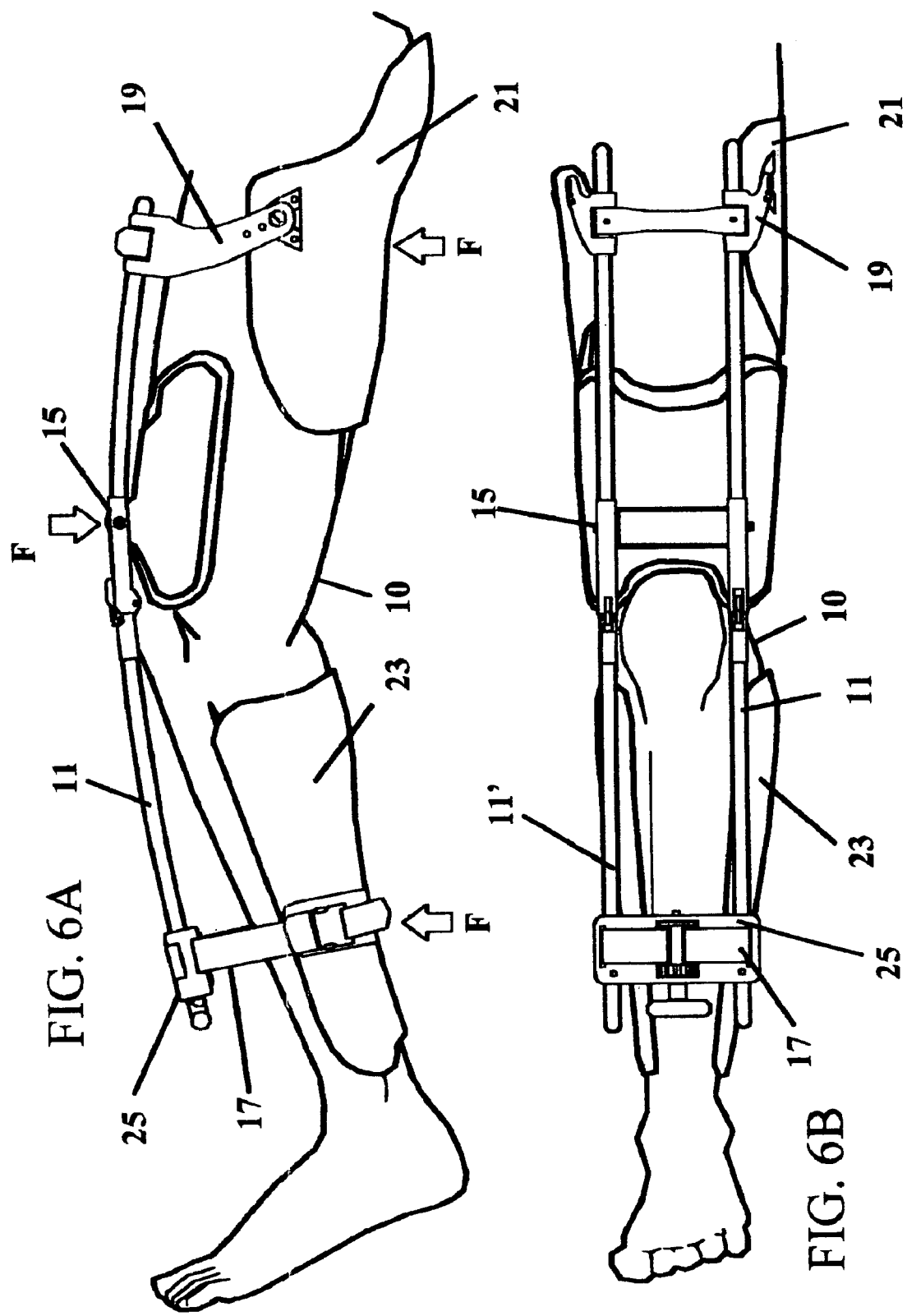
FIGS. 6A and 6B illustrate side and top views, respectively, of the splint of the present invention while under stress.
Figure 7:
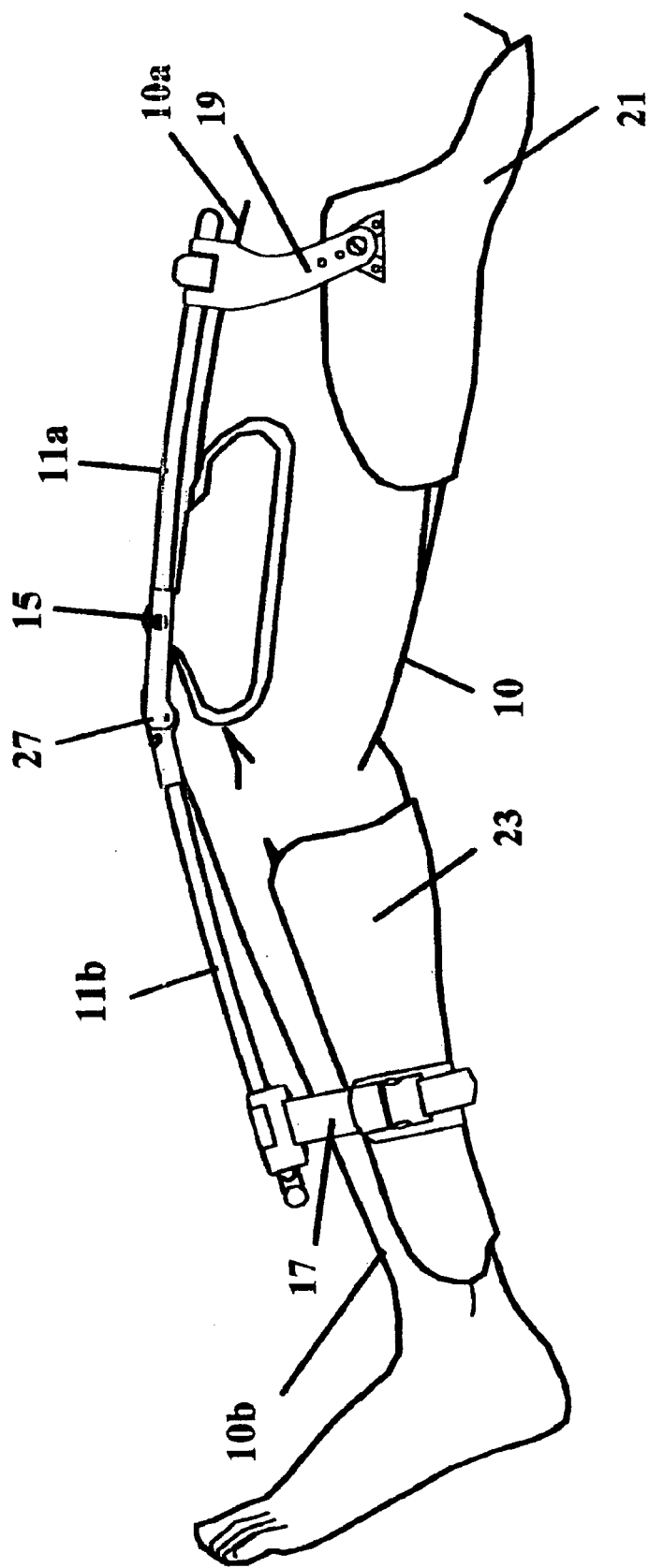
FIG. 7 is a side view of the splint of the present invention adjusted to maintain close limb alignment under tension enabled by the use of a unique locking hinge.

Referring now to FIGS. 6A and 6B, the splint device of the present invention comprises one or more flexible support members 11 and 11' oriented superior to the surface of the limb or digit 10. The flexible support members 11 and 11' attach to a fulcrum point 15 located superior and in proximity to the limb joint (e.g., knee in the illustrations), and when placed under tension transfer force F via attachments 17 and 19 to contact pads 23 and 21, respectively, on the opposing surface of the upper and lower portion of the limb or digit 10. A mechanical tension adjustment mechanism 25 allows force F to be adjusted and held incrementally. Referring to FIG. 7, an adjustable locking hinge 27 located between the upper 11a and lower 11b portion of the flexible support member 11 permits angular adjustment to allow the upper and lower portions of the flexible support member to align with the upper 10a and lower 10b portion of the limb 10 while retaining the flexible properties of the flexible support member 11. Details of the lockable hinge 27 are amplified further hereinbelow.

Figure 8:
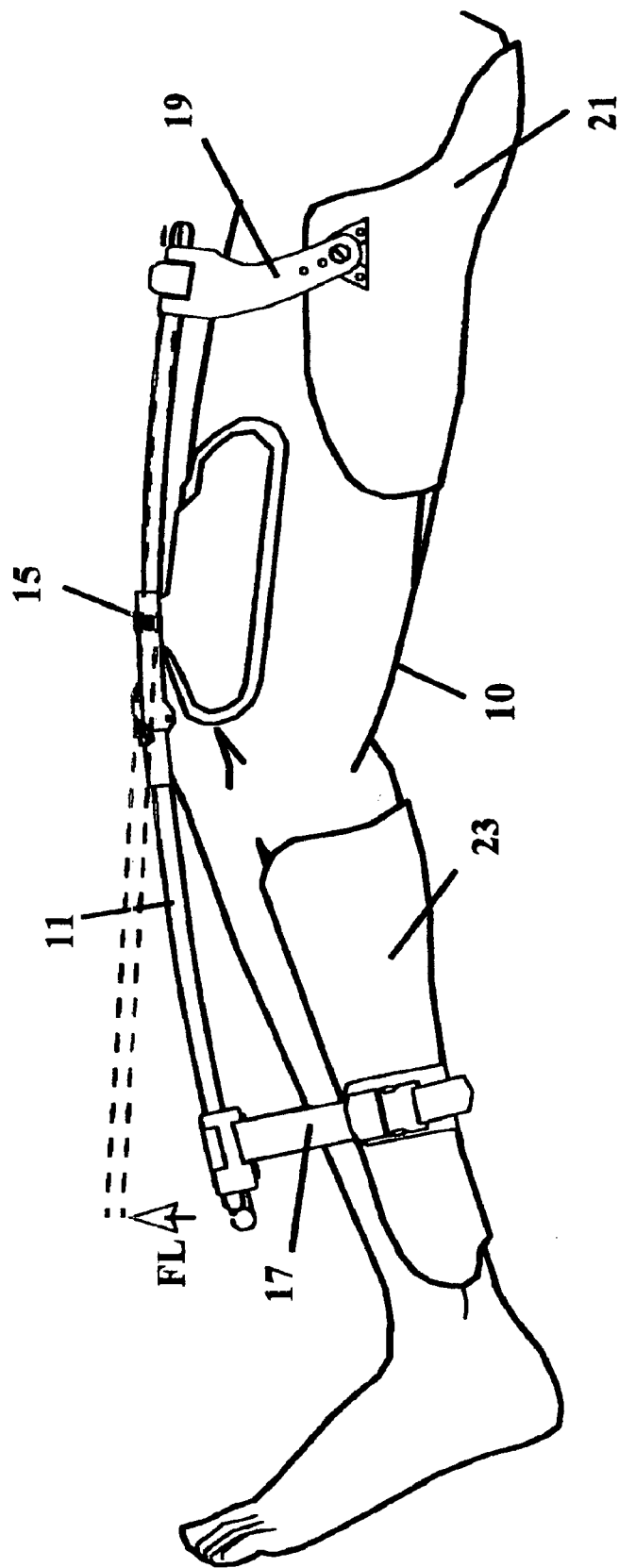
FIG. 8 is a side view of the splint of the present invention, again under tension, which illustrates the range of motion of the flexible supports from their relaxed state.

Referring now to FIG. 8, the orientation of the flexible support member 11 and fulcrum point 15 arrangement superior to the limb or digit 10 is shown. This arrangement allows flexion FL of the structural members in a linear path consistent with the natural range of motion of the limb or digit 10.

The specific improvements due to flexible support members 11 and 11' include use of composite, metallic, plastic or other like material in any convenient cross section or dimension in order to provide the desired physical properties of compression, tension and flexion required. Physical properties of the flexible support members 11 and 11' provide fully adjustable tensioning force for dynamic splinting applications, thereby eliminating the need for separate tensioning components such as springs or elastic materials. Moreover, the flexible properties of the members 11 and 11' continue to provide tension over a dynamic range as the soft tissue stretches. Flexible properties of these members also provide a shock absorbing quality, thereby reducing the chance of soft tissue damage frequently caused by high onset rate of dynamic forces. The flexible properties of the members 11 and 11' facilitate ambulatory rehabilitation, thereby providing an adjustable level of support and flex compatible with natural stride geometry.

Referring now to FIGS. 9A and 9B, orientation of the flexible support members 11a and 11a' (FIG. 9B, and 11b and 11b' in FIG. 9A) superior to the limb 10 in a suspension sling arrangement formed by the upper support pad 21 (FIG. 9B) and lower support pad 23 (FIG. 9A). Attachment 19, as shown in FIG. 9B, is shaped in the form of a yoke, which is captured by fixed cross member 16 allowing rotation R around the support members 11a and 11a' while providing support between the support member 11a or 11a' and the support pad 21. This suspension sling arrangement allows lateral movement LM of the limb and splint for proper alignment, thereby preventing distortion and misalignment stresses on the joints. Use of the structural fulcrum arrangement in proximity and superior to the affected joint more effectively transmits force and distributes pressure in a desired orientation to the soft tissues.

This structural orientation places upper limb portion 10a and lower limb portion 10b of the limb 10 in a unique suspension sling type configuration, thereby allowing splint movement LM to self-align to the limb geometry. Moreover, this self-alignment ensures force is applied only in the natural plane of limb motion, thereby effectively eliminating joint misalignment and stresses associated with splint distortion found in the prior art.

Figure 10:
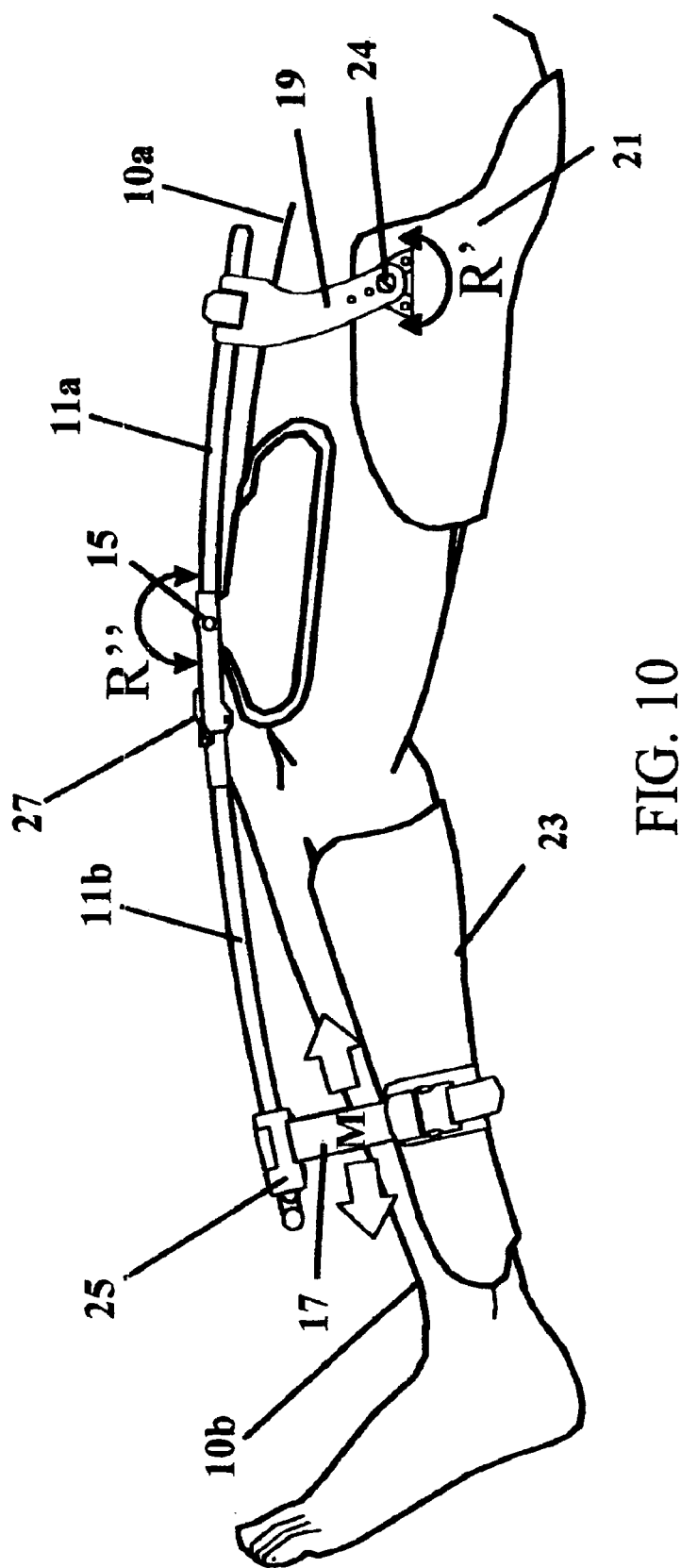
FIG. 10 is a side view of the splint of the present invention illustrating the self-alignment nature of the floating contact pads and the fulcrum point about an arc of rotation R.

Referring now to FIG. 10, a side view of the splint of the present invention illustrating the self-alignment nature of the floating contact pads and the fulcrum point 15 about an arc of rotation R" is shown. The upper limb portion 10a, lower limb portion 10b, and fulcrum point 15 contact pad attachment points are designed to rotate (R") about the fulcrum point 15, thereby allowing automatic limb alignment for optimal distribution of pressure over the entire surface area of the contact pads. The fork shaped configuration of the upper attachment 19 allows rotation R' and lateral movement while preventing longitudinal movement of the support pad 21, thereby ensuring proper splint alignment is maintained. The suspension sling arrangement of the lower attachment 17 further allows longitudinal movement M of the lower contact pad 23, thereby preventing stress on the soft tissues and joints. A button and slide receiver fastening 24, joining the upper attachment 19 to the support pad 21, allows easy donning or removal of the splint while preserving the ability to rotate as required.

Figure 11:
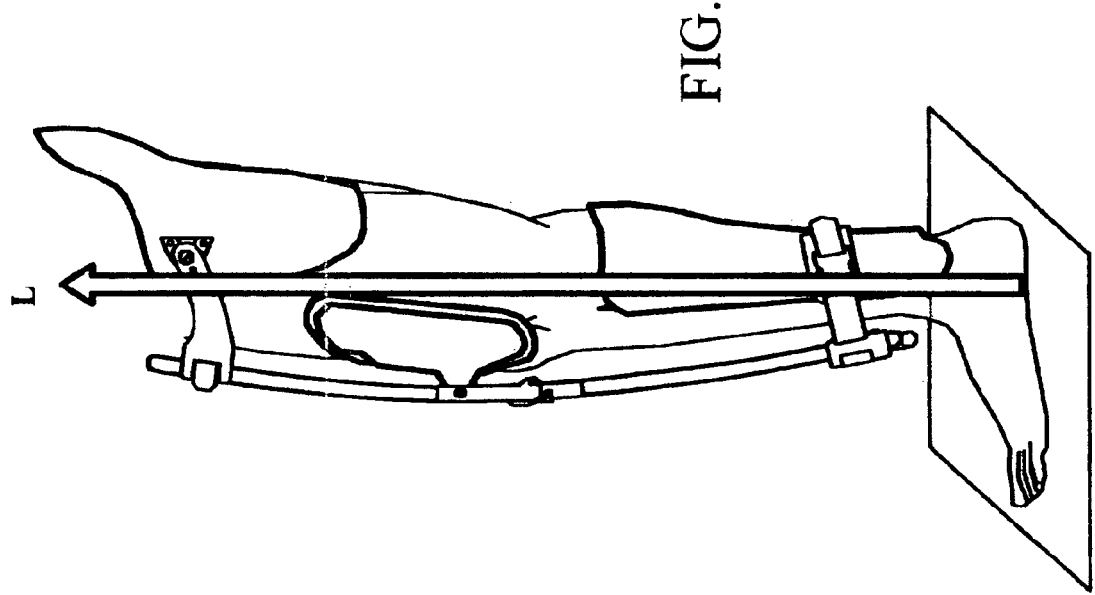
FIG. 11 is a side view of the splint of the present invention illustrating a patient wearing the splint while standing.

Referring now to FIG. 11, unique structural orientation enhances weight-bearing therapy by augmenting soft tissue deficiencies while allowing the weight bearing load L a path to be transported completely through the limb skeletal structure.

Figure 12A:
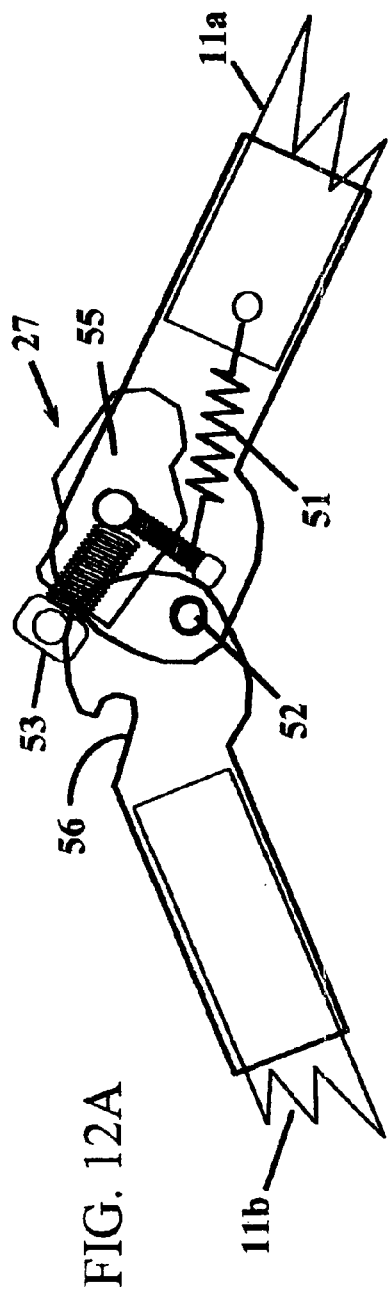
FIGS. 12A, 12B and 12C illustrate the hinge in an open to unlocked position, a locked straight position and a locked angle position, respectively.
Figure 12B:
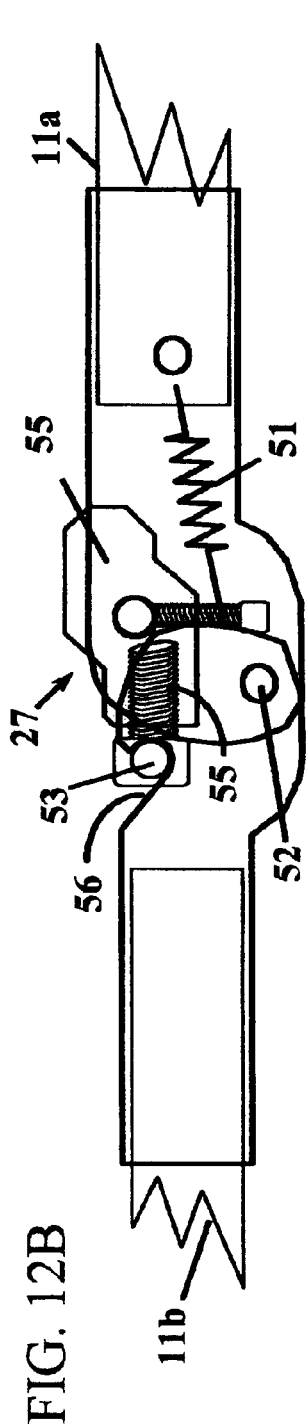
Figure 12C:
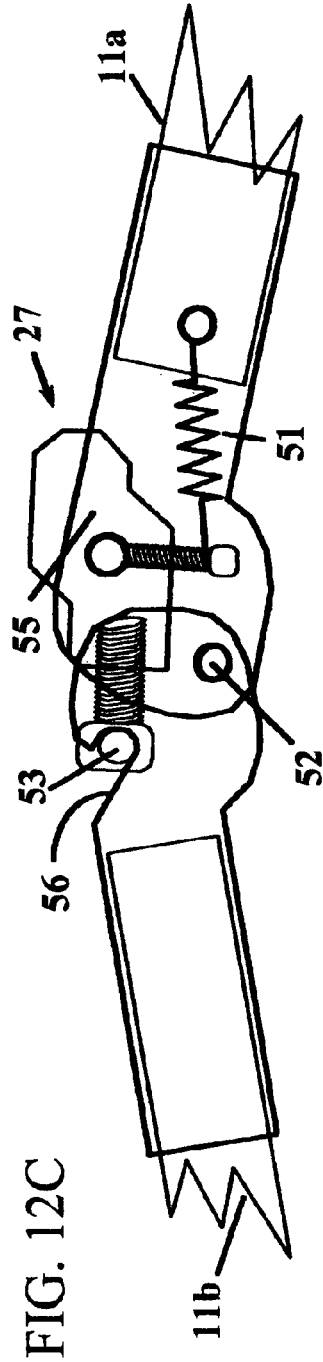
Figure 13B:
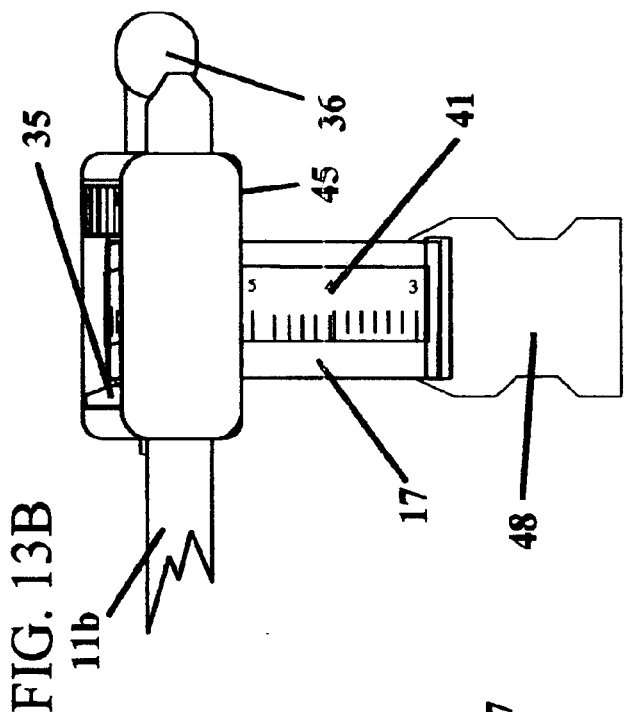
FIGS. 13A, 13B and 13C illustrate the top, side and end views, respectively, of the unique adjustable dynamic tension component affixed to the lower flexible support of the splint of the present invention.
Figure 13A:
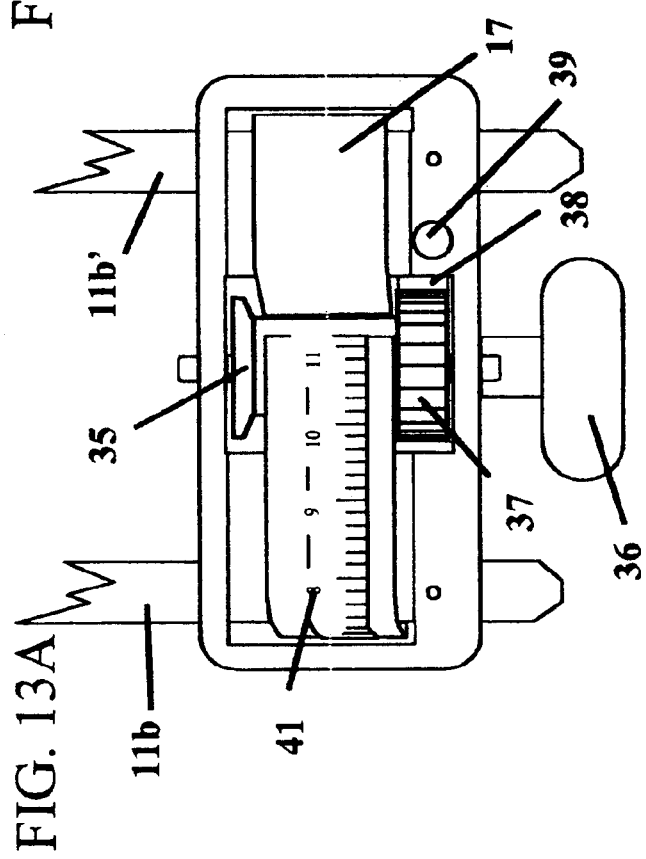
Figure 13C:
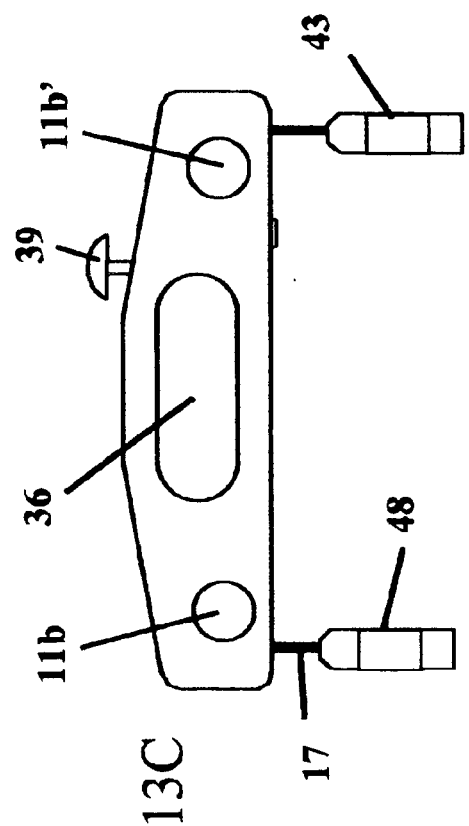

With reference now to FIGS. 12A, 12B and 12C the hinge 27 is shown in an open position, a locked and straight position and a locked and bent position, respectively. The hinge 27 is located between the upper portion 11a and lower portion 11b of the structural members 11 and 11'. The hinge 27 enhances the splint utility and adaptability. First, in the open position the hinge 27 allows the splint to be easily installed on a user. That is, as shown in FIG. 12A the hinge 27 allows the splint to articulate through the range of motion of the limb. When the splint is extended to a straight position the hinge 27 locks into place, as will be amplified hereinafter. An adjustment is provided in the hinge 27, which allows for an angular adjustment of the splint in order to maintain the full static tension properties while maintaining proximity and alignment of the upper 11a and lower 11b portions of the structural members 11 and 11' with upper and lower portions of the limb 10, respectively.

Referring to the open position of the hinge 27 as shown in FIG. 12A, the structural member portion 11a has attached thereto a block 55 having a threaded opening therein for receiving a T-shaped lock screw 53. The screw 53 may be adjusted for length (which adjusts the angle of the splint when locked) by screwing it in or out. A spring 51 biases the block 55 into position. The upper portion 11a and the lower portion 11b are coupled together by a pin 52, which allows these portions to flex in a hinge-like manner. When the two portions are flexed into a straighter position the cap of the T-shaped lock screw 53 engages a slot 56 on the lower portion 11b, which locks the two portions together as shown in FIG. 12B. When the T-shaped lock screw 53 is screwed out, thereby extending the length thereof from the block 55, the structural member portions 11a and 11b will lock in a fixed angled position as shown in FIG. 12C.

With reference now to FIGS. 13A, 13B and 13C top, side and end views of the unique adjustable dynamic mechanical tension component 25 is shown affixed to the lower flexible support of the splint. This tension component is affixed to the lower flexible support members 11b and 11b' and allows micro adjustable tension to be applied to the splint when attached to a user. Lower attachment strap 17 is wound on a tension spool 35 by rotation of a T-handle 36 to increase splint tension. A conventional ratchet 37 and pawl 38 prevents unwinding until a ratchet release pin 39 is depressed. Graduated markings 41 are permanently affixed to the strap 17 for measurement of the tension applied. Fastenings 43 and 48 allow rapid connection of the attachment strap 17 to the lower contact pad 23. Accordingly, tension settings are reliably replicated over successive therapy sessions. Tension may be fully adjusted without release or interruption while the splint is under tension.

As may be seen from the discussion hereinabove, there are numerous specific improvements due to the modular design of the present invention. For example, the selection from a range of individual component sizes, which may be based upon a patient's physiology, ensures a comfortable fit. The length, material and cross section of the flexible support members 11 and 11' may be matched to the patient's individual size requirements. The fulcrum point 15, and the contact pads 21 and 23, may also be individually selected from a range of stock sizes for the best fit to an individual patient's physiology. Fully adjustable component configuration allows complete assembly and adjustment in a single fitting.

Referring again to FIG. 10, dynamic tension mechanism 25 and the upper attachment fitting may be adjusted longitudinally along the flexible support members 11 to the optimal position where they are retained in position by recessed set-screws (not shown). Finally, the relationship of upper and lower contact pads to the flexible support members may be adjusted by lengthening or shortening the attachment straps in order to optimize the configuration and comfort.

Figure 14:
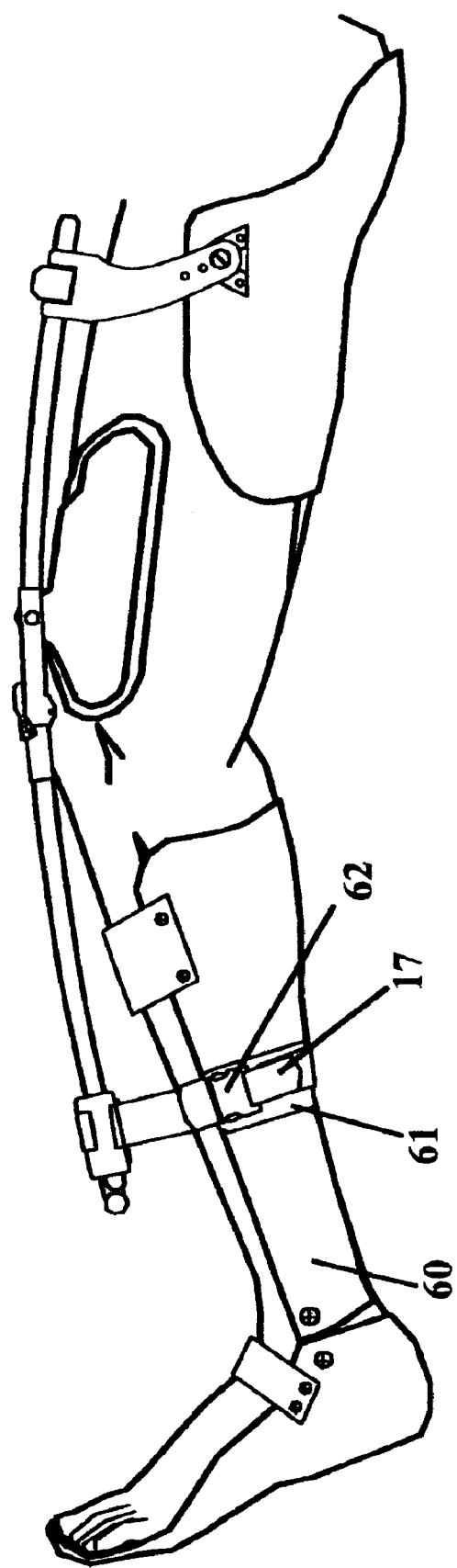
FIG. 14 is a side view of the splint of the present invention further including an Ankle Foot Orthotic (AFO) attached to the splint.

Moreover, it may be appreciated from the discussion hereinabove that there are specific improvements due to Ankle Foot Orthotic (AFO) compatibility. An example of this may be seen with reference to FIG. 14, wherein a view of the splint of the present invention is shown incorporating an AFO 60. Note that the AFO 60 is readily substituted for the lower contact pad 23. Adhesive backed loop fastenings 61 affixed to the AFO 60 retains the lower attachment strap 17 in proper position via an attached hook fastener 62. Hook and Loop fasteners allow rapid conversion of the splint for use with or without the AFO 60.

Figure 15:
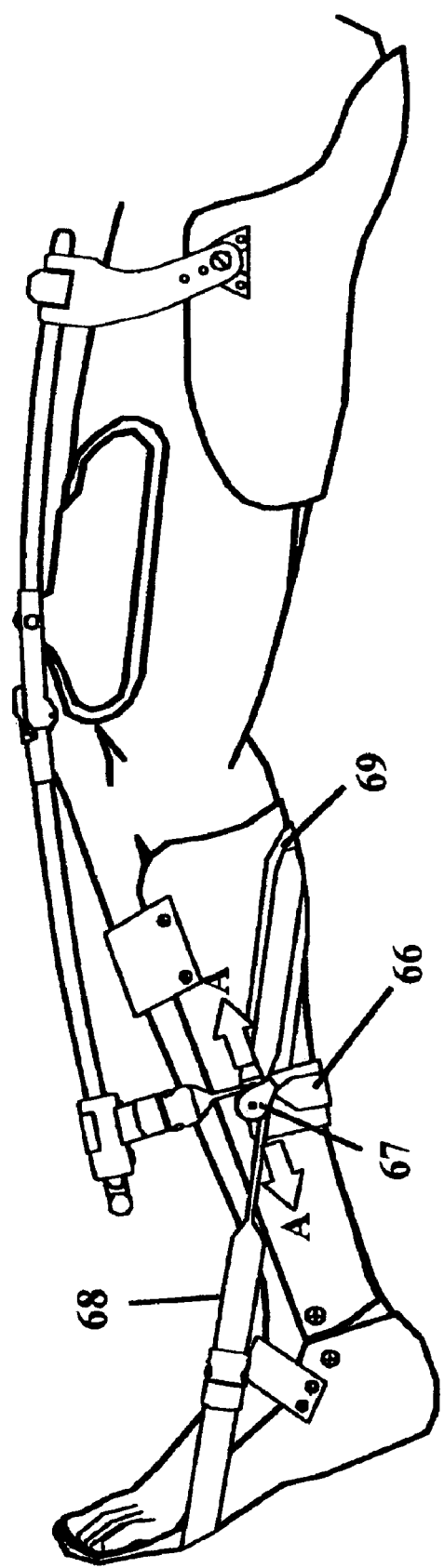
FIG. 15 is a side view of the splint and the AFO shown in FIG. 14, further including an optional module for translating forces for reduction of heel cord contraction.

Referring now to FIG. 15, an optional module translates force for reduction of heel cord contractures. The lower attachment of a dynamic tension module is fastened to an adjustable toe strap 68. The orthopedic splint includes an adjustable toe strap coupled between the toe of the ankle foot orthotic and the calf section of the ankle foot orthotic. Force is translated to the desired orientation via a pulley 67, which is held in position by an adjustable pulley anchor strap 66. The Anchor strap 66 is held in an adjustable position on the calf section of the AFO by hook and loop fastenings 69.

A unique feature simultaneously provides dynamic tension at both the knee and ankle joint, which increases effectiveness by preventing undesirable compensation at the knee resulting from force applied to lift the foot. This design allows full control of the ratio of the dynamic force directed at the ankle and knee joints by repositioning of the pulley anchor strap 66 through an adjustment range denoted by an arrow A.

Still other specific improvements offering ease of use are provided by the present invention. For example, the splint may be completely donned or removed by releasing only 2 quick release attachments on either the medial or lateral side of the limb 10. Ratcheting of the dynamic tension adjustment mechanism 25 allows complete one-handed tension adjustment with a simple turn of the tension T-handle 36. All adjustments and tension settings may remain fixed at the same position from the last use, thereby allowing a reliable duplication of the tension for serial or progressive therapies. Incremental graduations allow instant assessment of the amount and rate of therapy progress.

Figure 16:
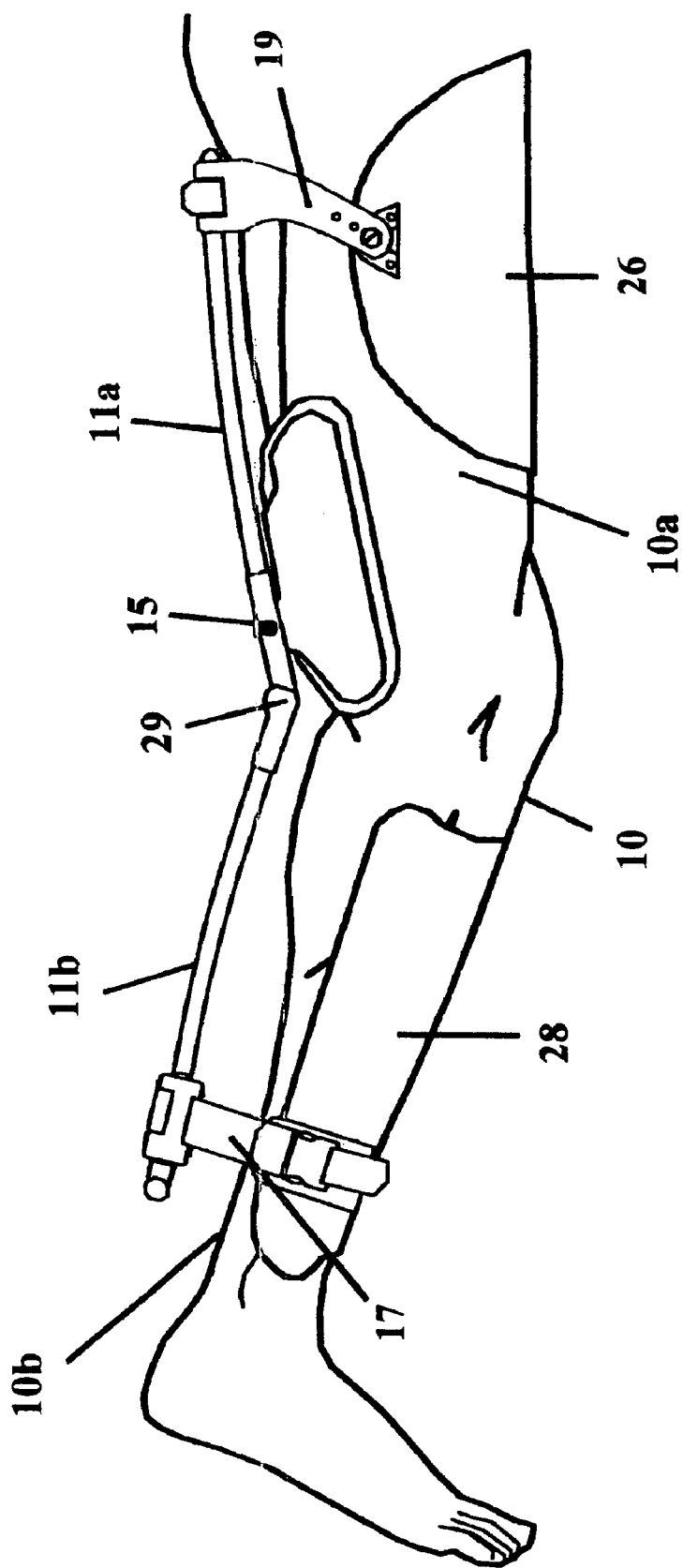
FIG. 16 is an elevation view of an alternate embodiment of the present invention.

It may be seen from the description above that the splint of the present invention has further applications for prevention or reduction of soft tissue contraction, which limits limb or digit extension range of motion. With reference now to FIG. 16, another use of the splint is in the prevention or reduction of soft tissue contraction limiting limb or digit flexion range of motion. Flexion contracture is treated through the use of the previously-described splint components, such as flexible support members 11a and 11b, fulcrum 15, and, attachments 17 and 19. The upper flexible support member 11a and lower flexible support member 11b are held fixed in the desired angular orientation by a modified locking hinge 29. Appropriately contoured upper contact pad 26 and lower contact pad 28 components preserve the self alignment features inherent in the splint design as previously described.

Yet another use is the prevention or reduction of soft tissue contraction which limits limb supination or pronation range of motion. Still other uses include limb or joint immobilization. The splint may also be used as a replacement for conventional serial casting. Yet another use of the splint is for ambulatory support and rehabilitation. A still further use of the splint is in surgical limb positioning, or for post operative limb or digit positioning. Another use of the splint is in correcting foot drop due to soft tissue contraction, commonly known as heel-cord shortening. Yet another use of the splint is in soft tissue augmentation for weight bearing therapies.

Although the invention has been described with reference to a specific embodiment, this description is not meant to be construed in a limiting sense. Various modifications of the disclosed embodiment as well as alternative embodiments of the invention will become apparent to one skilled in the art upon reference to the description of the invention. It is therefore contemplated that the appended claims will cover any such modifications of embodiments that fall within the true scope of the invention.

What is claimed is:

1. For a patient having a limb including an upper limb, a lower limb and a joint therebetween, an orthopedic splint for therapeutically stretching the soft tissue of said limb, said orthopedic splint comprising:
    a. a flexible support member having a distal end and a proximal end thereof;
    b. a first contact pad rotatably attached to the proximal end of said flexible support member and being disposed for distributing load to the underside of said upper limb;
    c. a second support pad attached to the distal end of said flexible support member and being disposed for distributing load to the underside of said lower limb; and,
    d. a third support pad attached as a fulcrum disposed near the center of said flexible support member and being disposed for distributing load to the topside of said limb and in close proximity to said joint, thereby providing therapeutic traction to said limb while placing said limb in a self-aligning suspension sling arrangement.

2. The orthopedic splint as in claim 1 wherein said flexible support member comprises a pair of composite material rods.

3. The orthopedic splint as in claim 1 wherein said flexible support member is formed of metal.

4. The orthopedic splint as in claim 1 wherein said flexible support member is formed of spring steel.

5. The orthopedic splint as in claim 1 further comprising a dynamic tension adjustment mechanism attached between said distal end of said flexible support member and said second support pad.

6. The orthopedic splint as in claim 1 further comprising a dynamic tension adjustment mechanism attached between said proximal end of said flexible support member and said first support pad.

7. The orthopedic splint as in claim 1 further comprising a dynamic tension adjustment mechanism attached between said third support pad and the fulcrum point of said flexible support member.

8. The orthopedic splint as in claim 1 further including a hinge in said flexible support member disposed in close proximity to said joint and said hinge including a lock for setting said flexible support member in a straight position.

9. The orthopedic splint as in claim 8 wherein said hinge lock includes an angular adjustment for setting said hinged flexible support member at a preferred angle.

10. For a patient having a leg including an upper leg, a lower leg, and a knee therebetween orthopedic splint for therapeutically stretching the soft tissue of said leg, said orthopedic splint comprising:
    a. a pair of flexible support members, each having a distal end and a proximal end thereof;
    b. a yoke rotatably attached at the proximal end of said flexible support members and being rotatable about the longitudinal axis of said flexible support members;
    c. a first contact pad rotatably attached to said yoke and being disposed for distributing load to the underside of said upper leg, said first contact pad being rotatable about an axis perpendicular to the longitudinal axis of said flexible support members;
    d. a second support pad attached to the distal end of said flexible support members and being disposed for distributing load to the underside of said lower leg; and,
    e. a third support pad attached as a fulcrum disposed near the center of said flexible support members and being disposed for distributing load to the topside of said leg and in close proximity to said knee, thereby providing therapeutic traction to said leg while placing said leg in a self-aligning suspension sling arrangement.

11. The orthopedic splint as in claim 10 wherein said flexible support members comprise a pair of composite material rods.

12. The orthopedic splint as in claim 10 wherein said flexible support members comprise spring steel.

13. The orthopedic splint as in claim 10 wherein said flexible support members are formed of metal.

14. The orthopedic splint as in claim 13 further comprising a dynamic tension adjustment mechanism attached between said distal end of said flexible support member and said second support pad.

15. The orthopedic splint as in claim 13 further comprising a dynamic tension adjustment mechanism attached between said proximal end of said flexible support member and said first support pad.

16. The orthopedic splint as in claim 13 further comprising a dynamic tension adjustment mechanism attached between said flexible support member and said third support pad.

17. The orthopedic splint as in claim 10 further including a hinge in said flexible support member disposed in close proximity to said joint and said hinge including a lock for setting said flexible support member in a straight position.

18. The orthopedic splint as in claim 17 wherein said hinge lock includes an angular adjustment for setting said hinged flexible support member at a preferred angle.

19. The orthopedic splint as in claim 10 further including an ankle foot orthotic coupled to said distal end of said flexible support member.

20. The orthopedic splint as in claim 19 further including an adjustable toe strap coupled between the toe of said ankle foot orthotic and the distal end of said flexible support member.

21. For a patient having a limb including an upper limb, a lower limb and a joint therebetween, an orthopedic splint for therapeutically stretching the soft tissue of said limb, said orthopedic splint comprising:
    a. a flexible support member, each having a distal end and a proximal end thereof;
    b. a first contact pad rotatably attached to the proximal end of said flexible support member and being disposed for distributing load to a first side of said upper limb;
    c. a second support pad attached to the distal end of said flexible support member and being disposed for distributing load to the said first side of said lower limb; and,
    d. a third support pad attached as a fulcrum disposed near the center of said flexible support member and being disposed for distributing load to the opposing side of said limb and in close proximity to said joint, thereby forming a lever and fulcrum arrangement for providing therapeutic traction to said limb.

22. The orthopedic splint as in claim 21 wherein said flexible support member comprises a pair of composite material rods.

23. The orthopedic splint as in claim 21 wherein said flexible support member comprises spring steel.

24. The orthopedic splint as in claim 21 wherein said flexible support member is formed of metal.

25. The orthopedic splint as in claim 21 further comprising a dynamic tension adjustment mechanism attached between said distal end of said flexible support member and said second support pad.

26. The orthopedic splint as in claim 21 further comprising a dynamic tension adjustment mechanism attached between said proximal end of said flexible support member and said first support pad.

27. The orthopedic splint as in claim 21 further comprising a dynamic tension adjustment mechanism attached between said flexible support member and said third support pad.

28. The orthopedic splint as in claim 21 further including a hinge in said flexible support member disposed in close proximity to said joint and said hinge including a lock for setting said flexible support member in a straight position.

29. The orthopedic splint as in claim 28 wherein said hinge lock includes an angular adjustment for setting said hinged flexible support member at a preferred angle.

* * * * *